United States Patent [19]

Ikayeva

[11] Patent Number: 5,320,601
[45] Date of Patent: Jun. 14, 1994

[54] METHOD FOR TREATMENT OF CHOLELITHIASIS AND CHRONIC HEPATO- AND CHOLECYSTOPATHIES SECONDARY TO SAID DISEASE

[76] Inventor: Liliya V. Ikayeva, ulitsa Ogneva, 9, apt. 50, Vladikavkaz, U.S.S.R.

[21] Appl. No.: 966,523

[22] Filed: Oct. 26, 1992

[30] Foreign Application Priority Data

Mar. 7, 1990 [SU] U.S.S.R. .............................. 4827909

[51] Int. Cl.$^5$ .................................................. A61M 31/00
[52] U.S. Cl. ....................................... 604/49; 128/898
[58] Field of Search ........................ 604/49, 28, 27; 128/898

[56] References Cited

U.S. PATENT DOCUMENTS

| | | | |
|---|---|---|---|
| 3,962,420 | 6/1976 | Siedel et al. | 424/81 |
| 4,105,794 | 8/1978 | Drell et al. | 424/317 |
| 4,198,396 | 4/1980 | Seidel et al. | 424/81 |
| 4,205,086 | 5/1980 | Babayan | 424/312 |
| 4,264,583 | 4/1981 | Jandacek | 424/240 |
| 4,910,223 | 3/1990 | Hofmann | 514/552 |
| 5,171,570 | 12/1992 | Takemori et al. | 424/195.1 |

OTHER PUBLICATIONS

Nonoperative Removal of Gallstones from the Biliary Ducts Using External Drainage, by A. I. Nechai et al., 1987 Meditsina Publishers, Leningrad, pp. 24–26.

*Primary Examiner*—John D. Yasko
*Assistant Examiner*—Michael Rafa
*Attorney, Agent, or Firm*—Lilling & Lilling

[57] ABSTRACT

The present invention relates to medicine.

A method for treatment of cholelithiasis and chronic hepato- and cholecystopathies secondary to that disease consists in that the patient with concrements not in excess of 2 cm in size are instituted on the first day of treatment a diet which is not causative of deterioration of their general state, whereupon the patients' gastrointestinal tract is evacuated, a cholinolytic spasmolytic agent is administered, and tubage is performed, accompanied by oral administration of a vegetable oil; on the second day of treatment the patients are prescribed a meal of food which promotes a cholagogic effect, and abundant drink, whereupon the motor function of the intestine is stimulated until the concrements are eliminated.

8 Claims, No Drawings

METHOD FOR TREATMENT OF CHOLELITHIASIS AND CHRONIC HEPATO- AND CHOLECYSTOPATHIES SECONDARY TO SAID DISEASE

TECHNICAL FIELD

The present invention relates generally to medicine and more specifically to a method for treatment of cholelithiasis and chronic hepato- and cholecystopathies secondary to said disease. The invention can find application in gastroenterology for treatment of patients affected by cholelithiasis and exhibiting concrements sized up to 2 cm, as well as of those suffering from chronic noncalculous cholecystitis, cholecystopancreatitis, post-cholecystectomy and post-infectious hepatitis states, an incipient stage of hepatocirrhosis, and dyskinesias of the biliary tract.

BACKGROUND OF THE INVENTION

Cholelithiasis is a rather widespread disease accounted for by the formation of gallstones in the gall bladder and the biliary ducts.

One state-of-the-art method for surgical treatment of cholelithiasis is known to be in extensive use nowadays, wherein the principal surgical interference is cholecystectomy, that is, ablation of the gall bladder. Such a surgical procedure may be combined with extraction of concrements from the biliary ducts followed by external or internal drainage of the common bile duct. Some other operative interventions may also be performed (cholecystectomy, cholecystostomy). Surgery on the gall bladder and biliary ducts requires definite indications in patients for a surgical interference and is far from ensuring steady convalescence (owing to the residual concrements that have remained unidentified).

Known in the present state of the art are also some methods for conservative treatment of cholelithiasis by administering a variety of medicinal agents promoting the litholysis process in the gall bladder and biliary ducts. Thus, for instance, a method for nonoperative treatment of cholelithiasis involves chemotherapy with the drugs made on the basis of some bile acids, that is, chenodeoxycholic and ursodeoxycholic (cf. a textbook "Nonoperative removal of gallstones from the biliary ducts using external drainage" by A. I. Nechai et al., 1987, Meditsina Publishers, Lenigrad, pp. 24–26 (in Russian). However, administration of the aforesaid drugs requires a prolonged (up to one or two years) treatment course. Moreover, the method discussed above is applicable only for dissolving small calculi of a definite nature, a positive result of treatment being noted only in 26 percent of the treated patients.

SUMMARY OF THE INVENTION

It is a principal object of the present invention to provide a highly efficient nonoperative method of treatment.

It is another object of the present invention to reduce the treatment period.

It is one more object of the present invention to avoid any side effects on patient's organism.

The foregoing principal and further objects of the invention are accomplished due to the fact that the herein-disclosed method for treatment of cholelithiasis and chronic hepato- and cholecystopathies secondary to said disease, according to the invention, consists in that a patient exhibiting the concrements measuring under 2 cm, is instituted on the first day of treatment a diet that is not causative of deterioration of patient's state, then the patient's gastrointestinal tract is evacuated, a cholinolytic spasmolytic agent is administered, and tubage is carried out, accompanied by oral administration of a vegetable oil. On the second day of treatment the patient is given a meal promoting a cholagogic effect, and abundant drink, whereupon the motor function of the intestine is stimulated until the concrements are eliminated. To attain the best therapeutic effect, the patient is administered preferably a 0.1-percent atropine solution intramuscularly as the aforesaid cholinolytic spasmolytic drug, while used as a vegetable oil is olive oil in an amount of 250 to 300 g. Tubage is carried out preferably for 3.5 to 4 hours. It is expedient that oatmeal porridge be given to the patient on the second day of treatment as a cholagogic meal.

Stimulation of the motor function of the intestine is expedient to be effected by combining physical exercise and warm water enemas. Whenever necessary the aforesaid treatment course may be repeated. With a view to normalization of the gastrointestinal tract within the post-treatment period, it is recommended that the patient is prescribed a milk-and-vegetable diet for a period of two weeks, as well as ingestion of mineral water and administration of a vegetable oil in a dose of one tablespoonful three times a day before meals. Besides, physical exercise is also instituted.

The disclosed method is simple in use, gives a steady clinical effect within a minimum treatment period, i.e., two days, is not onerous to the patient, and produces no side effects on patient's organism. The present method is instrumental in extracting the concrements from biliary and hepatic ducts of I–II–III orders, as well as from the gall bladder. As a result of treatment, concrements of various nature and in various amounts are eliminated, having the size of up to 2 cm. 80 percent of the patients exhibited positive results of treatment after a single course (for two days), while in 20 percent of the patients, after repeated treatment courses. Recovery sets in 99.8 percent of patients.

The method of the present invention is featured by a high percentage of convalescent patients treated for diseases secondary to cholelithiasis, such as cholecystopancreatitis, the post-cholecystectomy state, chronic noncalculous cholecystitis, the state following the sustained infectious hepatitis, and an incipient stage of hepatocirrhosis.

DETAILED DESCRIPTION OF THE INVENTION

The herein-disclosed method is carried into effect as follows. A patient exhibiting concrements not in excess of 2 cm in size (irrespective of their nature and amount) is instituted on the first day of treatment a diet not affecting adversely his/her general state, e.g., light meal consisting of tea and a rusk, followed by semolina gruel or kefir. Three hours later the gastrointestinal tract is epurated by an enema with water at 25° to 30° C; another 2 or 3 hours later the patient is administered intramuscularly a cholinolytic spasmolytic agent, e.g., atropine, platyphylline, or some other, preferably atropine as a 0.1-percent solution. Then the patient ingests 250 to 300 g of a vegetable oil, preferably olive oil, while in the right lateral decubitus with a heater in the region of the right hypochondrium. Then the patient is subjected to a probeless tubage for 3.5 to 4 hours. On the second day of treatment the patient is given a meal producing a cholagogic effect, e.g., oatgroats gruel, and abundant drink. Then for the entire day the patient is subjected to stimulation of the motor function of the intestine, preferably by combined physical exercise of the muscles of the trunk, abdominal tension and diaphragm and warm water enemas (up to 6 or 9 times) at one-hour interval. The result is the extraction of concrements.

The treatment is carried out within a remission period, since during the period of exacerbation of the morbid process the mucosa of the gall bladder and biliary ducts is edematous and infiltrated with a fibrin deposit. This narrows the lumen of the biliary duct and impedes outflowing of the bile and dislodging of the calculi. Institution of a diet and an evacuant enema to the patient on the first day of treatment promotes activation of the evacuatory function of the gastrointenstinal tract, as well as of the biliary passage. Administration of a cholinolytic spasmolytic agent in combination with probeless tubage activates choleresis and elimination of concrements. With the presence of concrements in the gall bladder and biliary ducts the inspissated congestive bile acquires a pastelike consistency, the calculi get coated with mucus and a fibrinous deposit and stuck together with one another and with the walls of the gall bladder and biliary ducts, which still more interferes with bile effluence and dislodging of concrements. Ingestion of a vegetable oil, e.g., the olive oil results in dissolving of mucus and fibrinous films, thinning of inspissated bile and softening of the concrements, whereby their mobility (slidability) is increased. Besides, the vegetable oil produces an emollient effect so that the tissues which has got in contact with the oil become more elastic, and the inflamed tissues become less tensioned. Higher secretion and stronger peristalsis ensue as well.

The method disclosed herein has passed clinical trials in a total of 390 patients. Steady recovery was attained in 88 percent of the patients after a single treatment course. Further 11.5 percent of the patients required from two to six treatment courses, and only in two cases (0.5 percent) the treatment proved to be futile. The disclosed method enables concrements to be dislodged completely, the bilirubincalcium formations inclusive. The present method is many times more efficient as compared with the now-existing methods of chemotherapy of cholelithiasis, including the heretofore-known method of treatment with chenodeoxycholic and ursodeoxycholic acids, wherein positive results of treatment were noted only in 26 percent of the patients and a treatment course lasted for one to two years, while the concrements are of small size and of a limited nature. The efficiency of the disclosed method is confirmed by the findings of ultrasonic and radiographic methods of examination and by a good general state of patients.

To promote understanding of the present invention, given below are the following examples of clinical trials of the method disclosed herein.

EXAMPLE 1

Male patient A., 35 was admitted with complaints of continuous moderate pain in the right hypochondrium which periodically took a paroxysmal character and was accompanied by nausea and bitter sensation in the mouth. Considered himself ill for five years since the onset of paroxysmal pain in the right hypochondrium, nausea, vomiting, and elevated body temperature. Clinicoradiologic analysis: calculous cholecystitis. The borders and structure of the liver are found to remain invariable upon ultrasonic examination. The gall bladder is not visualized clearly and is found to be filled with concrements having a diameter of up to 1.5 cm. The pancreas remains unaffected. A general patient's state is satisfactory. On palpation pronounced painfulness of the skin in the region of the gall bladder and cutaneous hypertension. Ortner's sympton weakly positive. The patient was given treatment according to the disclosed method. On the first day the patient was given a light meal at 8 a.m., that is, tea and a rusk; in 4 hours, 100 g of semolina gruel. In another 3 hours a cleansing enema with water at 25° to 30° C. was carried out. In another 3 hours 1 ml of a 0.1-percent atropine solution was administered intramuscularly, whereupon the patient ingested 250 g of olive oil and washed it down with a cup of coffee while in the right lateral decubitus with a heater in the region of the right hypochondrium. Then tubage was performed for a four-hour period. In the morning of the second day of treatment the patient was given a meal consisting of 250 g of oatgroats gruel and abundant drink. In two hours a series of five warm-water enemas was carried out at a one-hour interval in combination with physical exercises. As a result, a great number of gallstones were eliminated. On the third day the patient's general status improved. Pain in the right hypochondrium abated. Dislodging of the calculi 0.3 to 1.4 cm in diameter continued for six days. The patient was recommended to ingest olive oil for the next two weeks in a dose of one tablespoonful three times a day before meals, as well as a milk-and-vegetable diet, abundant drink, mineral water, and also to perform physical exercises.

A follow-up examination performed in two months demonstrated that the patients was practically healthy. No complaints were made. Control ultrasonic examination of the liver, gall bladder, and pancreas gave evidence that these organs were free from any pathologic changes.

EXAMPLE 2

Female patient Zh., 30, was admitted with complaints of severe pain in the right hypochondrium and referred pain in the right scapula and supraclavicular space. The patient has been suffering from cholecystopancreatitis for seven years. Her general state was of moderate severity. The cutaneous coverings rather pallid, the eyeball sclera icteric. A drastically painful tumorlike neoplasm was palpated in the right hypochondrium. Elevated body temperature. Diagnosis: calculous cholecystitis. A symptomatic treatment was carried out. Once an improvement in her general state had been attained, i.e., jugulation of pain, normalization of body temperature, the patient was subjected to cholecystography. The gall bladder abnormally enlarged and filled with concrements 1.0 to 1.6 cm in diameter. A treatment course was performed as follows. In the morning of the first day the patient was given a light meal, that is, tea and a rusk, and in 5 hours 50 g of semolina gruel. An evacuant water enema was made in three hours. In another three hours the patient was administered intramuscularly 1 ml of a 0.1-percent atropine solution. Then the patient ingested 250 g of olive oil and washed it down with a cup of coffee while in the right lateral decubitus with a heater in the region of the right hypochondrium. Tubage was carried out for 3.5 hours. In the morning on the second day the patient was given a meal, consisting of 250 g of oatgroats gruel and abundant drink. In two hours a series of six warm-water enemas was carried out at a one-hour interval in combination with physical exercises. As a result, a large number of gallstones 0.5 to 2 cm in diameter were eliminated.

The patient was recommended to adhere to the following regimen for the next two weeks: a milk-and-vegetable diet, abundant drink, warmed up mineral water, oral intake of olive oil in a dose of one tablespoonful three times a day before meals, and exercise therapy. The patient's general state is satisfactory, no complaints were made. In a month painfulness arose in the right hypochondrium and repeated cholecystography was carried out in the patients. The X-ray photo thus obtained displayed the gall bladder to have reduced by 65 or 70 percent as compared to the roentgenograms taken earlier, some sporadic concrements up to 0.8 cm in diameter being seen in the gall bladder. A repeated treatment course was performed. From the second till the seventh day of treatment isolated concrements were discharged in the intestinal contents. A control examination demonstrated that the patient was practically healthy.

EXAMPLE 3

Female patient B., 49 was admitted with the diagnosis of the post-cholecystectomy state. In six months after surgery for cholecystectomy the patient got troubled with pain in the right hypochondrium, occasionally accompanied by nausea and vomiting. The patient was more than once given both in-hospital and outpatient treatment. An ultrasonic examination was performed to demonstrate that the borders of the liver remained unchanged while concrements up 1.8 cm in diameter were detected in the biliary ducts.

The patient was given a treatment course according to the method disclosed herein. In the morning of the first day of treatment the patient was given a light meal, consisting of tea and a rusk, and in five hours also semolina gruel in an amount of 50 g. In three hours an evacuant water enema at a temperature of 25° to 30° C. After another three hours the patient was administered intramuscularly 1 ml of a 0.1-percent atropine solution, whereupon the patient ingested 300 g of olive oil and washed it down with a warm drink while in the right lateral decubitus with a heater in the region of the right hypochondrium. In the morning of the second day the patient was given a meal, consisting of 200 g of oatgroats gruel and abundant drink. In two hours a series of seven warm-water enemas was carried out at a one-hour interval in combination with physical exercises. On the second day of treatment up to 80 concrements having a diameter of from 0.9 to 1.8 cm were eliminated.

The patient was recommended to adhere to the following regimen for the next two weeks: a milk-and-vegetable diet, abundant drink, warm mineral water, ingestion of olive oil in a dose of one tablespoonful three times a day before meals, and respiratory gymnastics. A control examination demonstrated that a general state of the patient was good, no pain in the right hypochondrium occurred. On a repeated follow-up examination after an eleven-month period no complaints were made. The patient was considered apparently healthy.

What is claimed is:

1. A method for treatment of cholelithiasis and chronic hepato—and cholecystopathies secondary to said disease wherein concrements do not exceed 2.0 cm in size, comprising:
   a) instituting on the first day of treatment a diet which is not causative of deterioration of general state of a patient;
   b) evacuating gastrointestinal tract of a patient;
   c) administering a cholinolytic spasmolytic agent;
   d) performing tubage;
   e) orally administering a vegetable oil;
   f) prescribing on the second day of treatment a meal of food which promotes a chologogic effect, and abundant drink; and
   g) stimulating motor function of intestine until the concrements are discharged.

2. A method as claimed in claim 1, wherein a 0.1-percent atropine solution is administered to the patient intramuscularly as said cholinolytic spasmolytic agent.

3. A method as claimed in claim 1, wherein an olive oil in an amount of 250 to 300 g is used as said vegetable oil.

4. A method as claimed in claim 1, wherein said tubage is carried out for 3.5 to 4 hours.

5. A method as claimed in claim 1, wherein oatgroats gruel is used as said food promoting a cholagogic effect.

6. A method as claimed in claim 1, wherein stimulation of the motor function of the intestine is effected by combined physical exercises and enemas.

7. A method as claimed in claim 1, wherein said treatment course may be repeated whenever necessary.

8. A method as claimed in claim 1, wherein with a view to normalizing the function of the gastrointestinal tract, there are instituted to the patient for a two-week post-treatment period a milk-and-vegetable diet, mineral water and a vegetable oil in a dose of one tablespoonful three times a day before meals, and exercise therapy.

* * * * *